United States Patent [19]
Porret et al.

[11] 3,980,647

[45]*Sept. 14, 1976

[54] ADDUCTS OF POLYGLYCIDYL COMPOUNDS AND DIALKOXYPHOSPHONO-METHYL DERIVATIVES OF CYCLIC UREIDES

[75] Inventors: Daniel Porret, Binningen; Jurgen Habermeier, Pfeffingen, both of Switzerland

[73] Assignee: Ciba-Geigy Corporation, Ardsley, N.Y.

[ * ] Notice: The portion of the term of this patent subsequent to Mar. 23, 1993, has been disclaimed.

[22] Filed: Aug. 3, 1973

[21] Appl. No.: 385,616

[30] Foreign Application Priority Data

Aug. 10, 1972 Switzerland.................... 11845/72

[52] U.S. Cl............................ 260/248 NS; 260/260; 260/309.5

[51] Int. Cl.$^2$........................................ C07D 233/40
[58] Field of Search........ 260/309.5, 251 P, 248 NS

[56] References Cited
UNITED STATES PATENTS
3,894,016  7/1975  Habermeier et al. ......... 260/248 NS OTHER PUBLICATIONS
Nachbur, et al., C. A. vol. 73: 78494r (1970).

*Primary Examiner*—Natalie Trousof
*Assistant Examiner*—C. M. S Jaisle
*Attorney, Agent, or Firm*—Vincent J. Cavalieri

[57] ABSTRACT

Adducts of polyglycidyl compounds and cyclic ureides containing dialkoxyphosphonomethyl groups, such as 3-dialkoxyphosphonomethylhydantoins or 3-dialkoxyphosphonomethyldihydrouracils, and the use of the adducts for the manufacture of flameproof epoxide resins.

7 Claims, No Drawings

ADDUCTS OF POLYGLYCIDYL COMPOUNDS AND DIALKOXYPHOSPHONO-METHYL DERIVATIVES OF CYCLIC UREIDES

The invention relates to adducts of polyglycidyl compounds and cyclic ureides containing dialkoxyphosphonomethyl groups, such as 3-dialkoxyphosphonomethylhydantoins or 3-dialkoxyphosphonomethyldihydrouracils, and the use of the adducts for the manufacture of flameproof epoxide resins.

In order to manufacture flameproof plastics based on epoxide resin it has hitherto been necessary either to add flameproofing agents to the plastics, in which case the amounts required to achieve a good flameproofing action impair other properties of the plastics, or it was possible to use epoxide resins containing flameproofing groups. However, where epoxide resins containing phosphorus were concerned, these could only be manufactured with difficulties, since the addition of the phosphite to the epoxide compounds takes place incompletely (compare Swiss patent Specification No. 456,949). The adducts according to the invention, the manufacture of which takes place with high yield, give plastics which in spite of relatively small amounts of phosphorus possess very good flame resistance. The latter is better than that of the products described in the Swiss patent specification mentioned.

These new adducts are reaction products, containing epoxide groups, of polyglycidyl compounds and compounds of the formula I

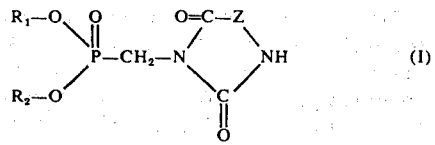

wherein Z denotes a nitrogen-free divalent radical which is required to complete a five-membered or six-membered ring and $R_1$ as well as $R_2$ each denote an alkyl or alkenyl group which can be substituted, for example by halogen, or together denote an alkylene group with 2 to 5 carbon atoms.

Z preferably represents a methylene group which can be substituted by alkyl groups with 1 to 6 carbon atoms, or represents a cycloalkylidene group, such as the methylene group or especially the 2,2-propylidene group, and also the n- or iso-propylmethylene group, the cyclohexylidene or cyclopentylidene group or an ethylene group optionally substituted by alkyl groups of 1 to 4 carbon atoms, such as the ethylene, 1,2-dimethylethylene, 2,2-dimethylethylene or 1-methyl-2-isopropylethylene group.

$R_1$ and $R_2$ preferably each denote an alkyl or alkenyl group with up to 4 carbon atoms, especially the methyl or ethyl group, but also the propyl, butyl, allyl, butenyl or monochloroethyl group.

The compounds of the formula I are obtained when compounds of the formula II

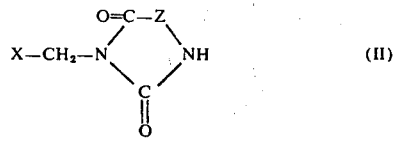

in which X denotes chlorine or bromine, are reacted with a trialkylphosphite of the formula III

wherein $R_3$ denotes an optionally substituted alkyl or alkenyl group.

For the reaction, which corresponds to a Michaelis-Arbusow reaction, the mixture is usually warmed for several hours to above 100°C, preferably 120°–160°C, whereupon $R_3X$ distills off. $R_3X$ is, for example, methyl chloride, ethyl chloride, butyl chloride or 1,2-dichloroethane.

The compounds of the formula II are obtained by reaction of the corresponding hydroxymethyl compounds with compounds which introduce chlorine or bromine, for example with acid halides, such as $SOCl_2$, $SOBr_2$, oxalyl chloride, $PCl_3$, $PCl_5$, $PBr_3$, $POCl_3$ or hydrogen chloride or hydrogen bromide.

The compounds of the formula I can also be obtained by reaction of compounds of the formula IV

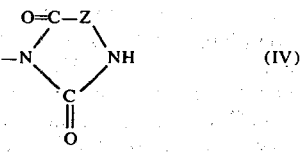

in which R' denotes a hydrogen atom, an alkyl group with 1 to 6 carbon atoms, a hydroxyalkyl group with 1 to 6 carbon atoms, an alkoxyalkyl group with 2 to 10 carbon atoms or an aryl group, with phosphorous acid dialkyl esters of the formula V

R' preferably represents hydrogen or the methyl, ethyl, hydroxyethyl, ethoxyethyl or phenyl group.

The reaction is appropriately carried out at elevated temperature, for example at 40 to 100°C, optionally with addition of an acid or basic catalyst, such as hydrogen chloride or triethylamine, and in the presence of solvents or diluents, such as alcohols or dioxane.

The compounds of the formula I are liquid to crystalline substances which are colourless in the pure state. They can be purified by recrystallisation or vacuum distillation.

The addition of the compounds of the formula I to the oxirane groups of the polyglycidyl compounds can be accelerated by customary catalysts, such as alkalis, amines, ammonium salts and alkali metal salts. The amounts of the compounds of the formula I, relative to the polyglycidyl compounds, can vary within wide limits, for example 0.05 to 0.5 molecule per epoxide group.

The addition of the polyglycidyl compounds to the compounds of the formula I initially takes place exclusively at a nitrogen atom possessing an active hydrogen atom, in the 1-position of the cyclic ureide. The secondary hydroxyl groups newly formed as a result of the addition reaction, and originating from the glycidyl groups, also possess reactive hydrogen atoms which can optionally subsequently also participate partly in the formation of the adducts. The adducts therefore are a mixture of chemical compounds which still possess free epoxide groups.

The phosphorus content of the adducts is preferably between 1 and 8% and the adducts are viscous to solid.

With regard to the flame resistance of the adducts, the reaction products of the compounds of the formula I with polyglycidyl compounds of cyclic ureides have proved advantageous.

The examples which follow describe the manufacture of the adducts from various polyglycidyl compounds with the hydantoin compounds A and B corresponding to the formula I. These compounds A and B are manufactured as follows:

A: 3-Dimethoxyphosphonomethyl-5,5-dimethylhydantoin

A mixture of 529 g of 3-chloromethyl-5,5-dimethylhydantoin (3.0 mols) and 447 g of trimethylphosphite (3.6 mols) is warmed over the course of 70 minutes to 150°C internal temperature (bath temperature 120°C–160°C), during the course of which vigorous reflux occurs. The methyl chloride produced in the reaction is condensed in a cold trap at −80°C in order to check the course of the reaction. After a further 2 hours' duration, the elimination of methyl chloride is complete and 150 g of methyl chloride (99.7% of theory) are obtained. The reaction product is freed at 90°C, in a water pump vacuum, of easily volatile constituents, such as excess trimethylphosphite, and is subsequently dried to constant weight at 0.1 mm Hg and 90°C.

780 g of a yellowish, crystalline crude product are obtained and this is purified by recrystallization from 500 ml of methyl ethyl ketone. 543.2 g of 3-(methanephosphonic acid dimethyl ester)-5,5-dimethylhydantoin [ ≙ (5,5-dimethylhydantoinyl-3)-methanephosphonic acid dimethyl ester ≙ 3-(dimethoxyphosphonomethyl)-5,5-dimethylhydantoin] (72% of theory) of melting point 112°–113.2°C are obtained.

| Elementary analysis: | |
|---|---|
| found: | calculated: |
| 38.4% C | 38.41% C |
| 6.2% H | 6.04% H |
| 11.3% N | 11.2% N |
| 12.7% P | 12.38% P |

The H-NMR spectrum is consistent with the following structure:

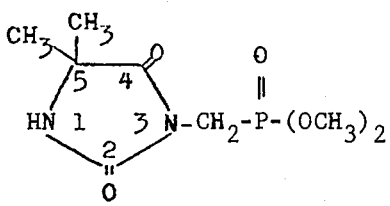

B. 3-Diethoxyphosphonomethyl-5,5-dimethylhydantoin 176.6 g of 3-chloromethyl-5,5-dimethylhydantoin (1.0 mol) are mixed with 199.5 g of triethylphosphite (1.2 mols) and the mixture is stirred for 5 hours at 126°–153°C internal temperature, during which 60.0 g of ethyl chloride (93.0% of theory) are split off. The resulting reaction product is freed of easily volatile constituents analogously to Example 1 and 273.3 g of crude product (98.1% of theory) are obtained. High vacuum distillation of the crude product yields 214.6 g of 3-(methanephosphonic acid diethyl ester)-5,5-dimethylhydantoin ( 3-diethoxyphosphonomethyl-5,5-dimethylhydantoin) (77.1% of theory) of boiling point 175°C/0.3 mm Hg and melting point 79°–82°C.

| Elementary analysis: | |
|---|---|
| found: | calculated: |
| 42.88% C | 43.17% C |
| 7.10% H | 6.88% H |
| 10.06% N | 10.07% N |
| 11.09% P | 11.13% P |

The H-NMR spectrum is consistent with the following structure:

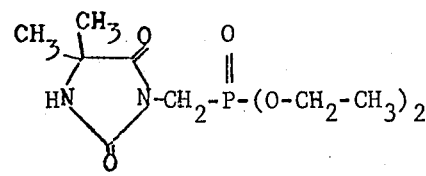

C. 3-(Di-n-butoxyphosphonomethyl)-5,5-pentamethylenehydantoin 216.7 g of 3-chloromethyl-5,5-pentamethylenehydantoin (1.0 mol) and 360.4 g of tributylphosphite are warmed to 140°C internal temperature (bath temperature 160°C) whilst stirring and 92.3 g of butyl chloride are distilled off over the course of 3 hours and 7 minutes; in the course thereof, towards the end of the reaction, a water pump vacuum is applied and the pressure is lowered to approx. 120 mm Hg. Thereafter the reaction product is concentrated on a rotary evaporator at 130°C and in a water pump vacuum. The mass is dried to constant weight at 130°C and 0.5 mm Hg. 396 g of a brown, partially crystalline crude product are obtained. A triple recrystallisation from hexane, ether/cyclohexane 1:1 and subsequently ether, in each case in the ratio of 1:2, leads to colourless crystals of melting point 86.6° to 87.6°C.

| Elementary analysis: | |
|---|---|
| found: | calculated: |
| 54.28% C | 54.53% C |
| 8.01% H | 8.35% H |
| 7.68% N | 7.48% N |
| 8.33% P | 8.27% P |

The product corresponds to the following formula:

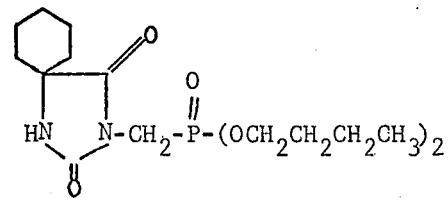

EXAMPLE 1

135.2 g of triglycidylisocyanurate having an epoxide content of 9.54 epoxide equivalents/kg, and 64.8 g of (5,5-dimethylhydantoinyl-3)-methanephosphonic acid dimethyl ester (manufactured as described under A) are stirred at 120°–160°C (bath temperature 168°C). After 14 minutes' reaction time, 0.5 g of 50% strength aqueous sodium hydroxide solution are added. The reaction is checked by taking samples and titrating the epoxide content. After 44 minutes' reaction time, the epoxide content is 5.82 epoxide equivalents/kg, and after 74 minutes it is 5.20 epoxide equivalents/kg. The reaction is complete after 84 minutes and the reaction product is cooled to room temperature by pouring out onto a metal sheet. A yellow, brittle, somewhat tacky resin having an epoxide content of 5.14 epoxide equivalents/kg is obtained in practically quantitative yield (theory = 200 g). The phosphorus content is 4.05% of P.

After fusing with a dicarboxylic acid anhydride, casting and curing in a mould at elevated temperature, the adduct gives castings having good mechanical properties and high flame resistance.

EXAMPLE 2

A mixture of 300 g of the industrially manufactured triglycidyl compound from 1,3-bis-(5′,5′-dimethylhydantoinyl-3′)-propan-2-ol, having an epoxide content of 6.1 epoxide equivalents/kg, 138.2 g (0.496 mol) of 3-(diethoxyphosphonomethyl)-5,5-dimethylhydantoin (manufactured as described under B) and 0.2 ml of 40% strength methanolic tetramethylammonium chloride solution is reacted at 142°–169°C internal temperature (bath temperature: 170°C). The course of the reaction is analogous to Example 1. After 17 minutes' reaction time the epoxide content is 3.87 epoxide equivalents/kg and after 27 minutes it is 3.67 epoxide equivalents/kg. The addition is complete after 42 minutes and the reaction product is cooled to room temperature by pouring out onto a metal sheet. 436 g of a solid, tacky, yellow resin (99.5% of theory), having an epoxide content of 3.43 epoxide equivalents/kg (calculated: 3.5 epoxide equivalents/kg) are obtained. The phosphorus content is 3.5% of P.

The IR spectrum shows, through the absence of the NH band (distinct NH band of the phosphonate at 3,422 cm$^{-1}$ before the addition) and through the presence of the OH band at 3,485 cm$^{-1}$, that the reaction has followed the desired course.

EXAMPLE 3

200 g of commercially available diglycidyl ether from bisphenol A, having an epoxide content of 5.3 epoxide equivalents/kg, 112.5 g (0.405 mol) of 3-(diethoxyphosphonomethyl)-5,5-dimethylhydantoin (manufactured as described under B) and 0.4 ml of 40% strength methanolic tetramethylammonium chloride solution are reacted at 145°–170°C internal temperature (bath temperature 160°–180°C) for 3 hours 55 minutes, whilst stirring. Working up takes place as described in Example 1. 310.5 g of a brownish, viscous resin (theory = 312.5 g) having an epoxide content of 1.93 epoxide equivalents/kg are obtained. The phosphorus content is 4.05% of P.

EXAMPLE 4

100 g of 1,3-diglycidyl-5,5-pentamethylenehydantoin (epoxide content: 6.95 epoxide equivalents/kg), 56 g (0.201 mol) of 3-(diethoxyphosphonomethyl)-5,5-dimethylhydantoin (manufactured as described under B) and 0.2 ml of 40% strength methanolic tetramethylammonium chloride solution are stirred for 55 minutes at 125°–164°C internal temperature. The mixture is cooled to room temperature and 150 g of a brownish, highly viscous resin (96.1% of theory) having an epoxide content of 3.15 epoxide equivalents/kg are obtained.

EXAMPLE 5

A mixture of 300 g of commercially available 3-(3′,4′-epoxycyclohexyl)-2,4-dioxaspiro(5,5) 9,10-epoxyundecane, having an epoxide content of 6.2 epoxide equivalents/kg, 203 g (0.729 mol) of 3-(diethoxyphosphonomethyl)-5,5-dimethylhydantoin (manufactured as described under B) and 0.8 ml of 40% strength methanolic tetramethylammonium chloride solution is reacted at 151°–176°C internal temperature (bath temperature 160°–186°C). After 1 hour 50 minutes, 1 ml of 40% strength methanolic tetramethylammonium chloride solution is added and after 370 minutes 0.5 ml of 50% strength aqueous sodium hydroxide solution is added. The reaction is complete after 490 minutes. After cooling, 500 g of a yellow-brown, solid resin (99.4% of theory) are obtained, having an epoxide content of 2.26 epoxide equivalents/kg (calculated: 2.25 epoxide equivalents/kg), a softening point of 78°C and a phosphorus content of 4.85% of P.

EXAMPLE 6

300 g of 1,3-diglycidyl-5,5-dimethylhydantoin, having an epoxide content of 7.85 epoxide equivalents/kg, 168 g (0.604 mol) of 3-diethoxyphosphonomethyl)-5,5-dimethylhydantoin (0.604 mol) (manufactured as described under B) and 0.8 ml of 40 % strength methanolic tetramethylammonium chloride solution are stirred for 82 minutes at 152°–166°C internal temperature. The procedure described in Example 1 is followed and 465 g of a yellow, clear, highly viscous resin (99.4% of theory) are obtained, having an epoxide content of 3.68 epoxide equivalents/kg (calculated: 3.73 epoxide equivalents/kg) and a phosphorus content of 4.06% of P.

EXAMPLE 7

300 g of an industrially manufactured triglycidyl compound from 1,3-bis-(5′,5′-dimethylhydantoinyl-3′)-propan-2-ol (epoxide content: 6.12 epoxide equivalents/kg), 220.1 g of 3-(di-n-butoxyphosphonomethyl)-5,5-pentamethylenehydantoin (manufactured as described under C) and 0.2 ml of 40% strength methanolic tetramethylammonium chloride solution are reacted at 161° to 170°C internal temperature. After 65 minutes' reaction time, the epoxide content is 2.81 epoxide equivalents/kg and after 125 minutes it is 2.62 epoxide equivalents/kg. The addition is complete after 3 hours and 15 minutes and the reaction product is isolated by pouring out onto a metal sheet. 316 g of a clear, brown solid resin (99.2% of theory) are obtained, having an epoxide content of 2.40 epoxide equivalents/kg and a phosphorus content of 3.4%. The softening point is 50°C.

Use example I 100 g of adduct manufactured according to Example 1 are stirred with 75.2 g of hexahydrophthalic anhydride at 120°C and the clear, yellowish mixture is poured into aluminium moulds of sizes 120 × 120 × 4 mm and 120 × 15 × 10 mm which are pre-warmed to 120°C.

Curing takes place in 2 hours at 120°C and 16 hours at 150°C. The castings thus obtained have the following properties:

| | |
|---|---|
| Flexural strength (VSM 77,103) | 9.0 kg/mm² |
| Deflection (VSM 77,103) | 3.3 mm |
| Impact strength (VSM 77,105) | 8.6 cmkg/cm² |
| Heat distortion point according to Martens (DIN 53,461) | 137°C |
| Inflammability according to CTM 20* | Level 1 (5") |

*CTM 20: Description of the test:

A horizontally clamped DIN standard bar (120 × 15 × 10 mm) of the plastic to be tested is exposed for 1 minute to the flame of a Bunsen burner supplied with town gas and inclined at 45° (burner orifice 9 mm, flame height with the burner vertical: 10 cm), so that the 15 mm wide surface of the test specimen is 3 cm above the upper edge of the burner and the end face is 1 cm, in a horizontal direction, from the lower edge of the burner.

Level 1 denotes that after removing the flame the bar does not continue to burn for more than 15 seconds. It is comparable with Category 2 of ISO/R 1,210 (burning time 0–15 seconds).

Use example II 100 g of adduct manufactured according to Example 2 and 50.2 g of hexahydrophthalic anhydride are cast and cured analogously to Example I.

| Test results: | | |
|---|---|---|
| Flexural stress: | (VSM 77,103) | 12.6 – 15.3 kg/mm² |
| Deflection: | (VSM 77,103) | 5.2 – 6.6 mm |
| Impact strength: | (VSM 77,105) | 10.0 – 10.5 cmkg/cm² |
| Water absorption: | (4 days/20°C) | 1.63% |
| " | (1 hour/100°C) | 2.59% |
| Inflammability according to ISO | | Category 2 (6" – 12") |

Use example III 100 g of adduct manufactured according to Example 5 and 33.1 g of hexahydrophthalic acid are processed analogously to Use Example I. The castings obtained give the following values:

| | |
|---|---|
| Inflammability according to CTM 20 | Level 1 (7") |
| Heat distortion point according to Martens (DIN 53,461) | 98°C |

Use example IV 100 g of epoxide compound manufactured according to Example 6 and 53.8 g of hexahydrophthalic anhydride are mixed at 120°C, poured into aluminium moulds pre-warmed to 120°C, analogously to Use Example I, and cured.

| Test results: | |
|---|---|
| Flexural strength (VSM 77,103) | 12.9 – 15.6 kg/mm² |
| Deflection (VSM 77,103) | 8.5 – 13.7 mm |
| Impact strength (VSM 77,105) | 12.8 – 20.8 cmkg/cm² |
| Heat distortion point according to Martens (DIN 53,461) | 107°C |
| Water absorption (4 days/20°C) | 0.21% |
| Inflammability according to CTM 20 | Level 1 (2") |
| Inflammability according to ISO: | Category 2 (3" – 6") |

Use example V 100 parts of the epoxide compound described in Example 7 and 34.9 g of hexahydrophthalic anhydride are stirred at 100°C to give a homogeneous melt, cast analogously to Use Example I and cured in 2 hours at 100°C, 2 hours at 120°C and 16 hours at 150°C.

| Test results: | |
|---|---|
| Flexural strength (VSM 77,103) | 8.8 – 10.8 kg/mm² |
| Deflection (VSM 77,103) | 3.3 – 4.4 mm |
| Impact strength (VSM 77,105) | 7.5 – 10.25 cmkg/cm² |
| Heat distortion point according to Martens (Din 53,461) | 70°C |
| Inflammability according to CTM 20 | Level 1 (1") |
| Water absorption (1 hour/100°C) | 2.21% |

We claim:
1. An adduct, containing epoxide groups, prepared by the reaction of triglycidylisocyanurate, and a compound of the formula

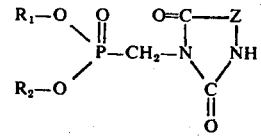

wherein Z is methylene, methylene substituted by alkyl of 1–6 carbon atoms, cyclohexylidene, cyclopentylidene, ethylene, or ethylene substituted by alkyl of 1 to 4 carbon atoms, and $R_1$ and $R_2$ each denote alkyl of 1 to 4 carbon atoms, alkenyl of up to 4 carbon atoms, or monochloroethyl, or together denote an alkylene of 2 to 5 carbon atoms, wherein the amount of phosphorous compound relative to the polyglycidyl compound in the adduct is from 0.05 to 0.5 molecule per epoxide group and wherein said reaction is conducted in the presence of a catalyst selected from the group consisting of alkalis, amines, ammonium salts and alkali metal salts.

2. The adduct according to claim 1 wherein said polyglycidyl compound is triglycidylisocyanurate, and said phosphorous compound is 3-(dialkoxyphosphonomethyl)-hydantoin wherein said alkoxy contains from 1 to 4 carbon atoms.

3. The adduct according to claim 2 wherein said polyglycidyl compound is triglycidyl isocyanurate and said phosphorous compound is (5,5-dimethylhydantoinyl-3)-methanephosphonic acid dimethylester.

4. Adducts according to claim 1, of the formula I, in which Z denotes the 2,2-propylidene group.

5. Adducts according to claim 1, of the formula I, in which Z denotes the cyclohexylidene group.

6. Adducts according to claim 1, of the formula I, in which $R_1$ and $R_2$ each denote an alkyl or alkenyl group with up to 4 carbon atoms.

7. Adducts according to claim 1, of the formula I, in which $R_1$ and $R_2$ denote the ethyl or methyl group.

* * * * *